US009052284B2

(12) United States Patent
Cao et al.

(10) Patent No.: US 9,052,284 B2
(45) Date of Patent: Jun. 9, 2015

(54) ASYMMETRIC FIELD ION MOBILITY SPECTROMETER

(71) Applicant: Nuctech Company Limited, Haidian District, Beijing (CN)

(72) Inventors: Shiping Cao, Beijing (CN); Qingjun Zhang, Beijing (CN); Zhiqiang Chen, Beijing (CN); Ziran Zhao, Beijing (CN); Yuanjing Li, Beijing (CN); Yinong Liu, Beijing (CN); Shuqiang Dong, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 0 days.

(21) Appl. No.: 14/128,894

(22) PCT Filed: Dec. 28, 2012

(86) PCT No.: PCT/CN2012/087797
§ 371 (c)(1),
(2) Date: Dec. 23, 2013

(87) PCT Pub. No.: WO2013/097758
PCT Pub. Date: Jul. 4, 2013

(65) Prior Publication Data
US 2014/0319337 A1 Oct. 30, 2014

(30) Foreign Application Priority Data
Dec. 28, 2011 (CN) .......................... 2011 1 0446360

(51) Int. Cl.
*H01J 49/26* (2006.01)
*G01N 27/62* (2006.01)

(52) U.S. Cl.
CPC ............ *G01N 27/624* (2013.01); *G01N 27/622* (2013.01)

(58) Field of Classification Search
USPC ......... 250/281, 282, 283, 290, 291, 292, 293, 250/294, 295, 296, 297, 298, 299
See application file for complete search history.

(56) References Cited

U.S. PATENT DOCUMENTS

2006/0097156 A1* 5/2006 Guevremont ................. 250/290

FOREIGN PATENT DOCUMENTS

| CN | 101063672 A | 10/2007 |
|---|---|---|
| CN | 202394834 U | 8/2012 |
| EP | 1 051 732 B1 | 4/2013 |

OTHER PUBLICATIONS

International Search Report for corresponding International Patent Application No. PCT/CN2012/087797 mailed Apr. 4, 2013.
Chinese Office Action for corresponding Chinese Patent Application No. 201110446360.0 mailed Feb. 4, 2015.

* cited by examiner

*Primary Examiner* — Nicole Ippolito
(74) *Attorney, Agent, or Firm* — Merchant & Gould P.C.

(57) ABSTRACT

The present invention discloses an asymmetric field ion mobility spectrometer. It comprises an ionization source, for generating ions; an electrode plate; a plurality of electrode filaments, arranged in opposite to and spaced apart from the electrode plate by an analysis gap, wherein a high voltage of electrical field is applied between the electrode plate and the electrode filaments to form an ion migration area, the electrode filaments used to collect the ions that do not pass through the ion migration area; and a collection electrode, disposed at a rear end of the ion migration area, and collecting the ions that have passed through the ion migration area. The present asymmetric field ion mobility spectrometer is capable of improving accuracy of identifying peak positions of the ions, reducing scanning time of DC voltage and types of compensation voltage, thereby increasing ion detection efficiency.

10 Claims, 4 Drawing Sheets longwise position of signal filaments longwise position of signal filaments

ASYMMETRIC FIELD ION MOBILITY SPECTROMETER

This application is a National Stage Application of PCT/CN2012/087797, filed Dec. 28, 2012, which claims the benefit of Chinese Patent Application No. 201110446360.0 filed on Dec. 28, 2011 in China and which applications are incorporated herein by reference. To the extent appropriate, a claim of priority is made to each of the above disclosed applications.

BACKGROUND OF THE INVENTION

1. Field of the Invention

The present invention relates to a technical field of ion migration, and more particularly to an asymmetric field ion mobility spectrometer.

2. Description of the Related Art

Asymmetric field ion migration is a new type of ion migration technique. It utilizes characteristic of mobility of charged molecular clusters varying with intensity of electrical field under the action of a strong electrical field, to identify corresponding molecules. Typically, an asymmetric field ion mobility spectrometer is composed of two parallel electrodes and a collection electrode. The parallel electrodes each have a length less than 10 mm, and a width less than 5 mm, with a spacing of 0.5 mm between them. The electrodes are formed by copper plated on two pieces of glass plates. Ionized molecules enter into the electrodes under the action of uniform gas flow, and only the charged molecules satisfying a specific condition can reach the collection electrode through a gap between the electrodes. One piece of electrode is grounded while the other piece of electrode is applied with pluses having amplitude up to approximate 1000V and a pulse width of dozens of nanoseconds, and at the same time is applied with a DC compensation voltage. Only the ions which satisfy a condition of $K1 \times t1 = K2 \times t2$ can pass the gap, wherein K1 is an ion mobility under the strong electrical field, t1 is a high voltage pulse width, K2 is an inherent mobility under a weak electrical field, and t2 is a weak electrical field pulse width. The aim of identifying substances can be achieved by scanning the different ions released by the DC compensation voltage.

However, the above described asymmetric field ion mobility spectrometer with parallel electrode plates cannot accurately distinguish peak positions of different ions. Therefore, there is a need to have an ion mobility spectrometer having a new electrode structure.

SUMMARY OF THE INVENTION

Therefore, it is an object of the present invention to solve at least one aspect of the above problems and defects in the prior art.

Accordingly, one object of the present invention is to provide an asymmetric field ion mobility spectrometer, which can accurately identify peak positions of different ions.

Another object of the present invention is to provide an asymmetric field ion mobility spectrometer, which can identify different ions under the same compensation voltage.

A further object of the present invention is to provide an asymmetric field ion mobility spectrometer, which can reduce scanning time of the DC voltage.

In accordance with one aspect of the present invention, an asymmetric field ion mobility spectrometer is provided, the asymmetric field ion mobility spectrometer comprising:

an ionization source, for generating ions;

an electrode plate;

a plurality of electrode filaments, arranged in opposite to the electrode plate and spaced apart from the electrode plate by an analysis gap, wherein a high voltage of electrical field is applied between the electrode plate and the plurality of electrode filaments to form an ion migration area, and the electrode filaments are used to collect the ions that do not pass through the ion migration area; and a collection electrode, disposed at a rear end of the ion migration area, and collecting the ions that have passed through the ion migration area.

Specifically, the plurality of electrode filaments can comprise at least a pair of reference filament and signal filament adjacent to each other, spaced apart from each other by a predetermined distance with a potential difference between them.

Further, the corresponding reference filament and signal filament in each pair of the reference filament and signal filament can be respectively connected to two ends of an inductive coupler on the same side via capacitance, so that a signal about the ions collected by each signal filament is extracted out from the other side of the inductive coupler.

Specifically, the corresponding reference filament and signal filament in each pair of the reference filament and signal filament can have a potential difference equal to or less than 5V between them.

Specifically, a potential of the reference filament is 0V, and a potential of the signal filament may be +5V or −5V.

Further, the asymmetric field ion mobility spectrometer can comprise a pair of introduction electrodes oppositely located at a front end of the ion migration area, and the ionization source is provided in a middle part of one introduction electrode in the pair of introduction electrodes.

Further, the analysis gap has a width of 0.5 mm, the diameter of the electrode filament is 0.1-0.3 mm and the distance between the respective adjacent electrode filaments is 0.1-0.5 mm.

Further, the electrode plate can be a copper plating layer which is plated on glass material or insulator, and the electrode filament is a copper filament or a copper filament plated on insulator.

Further, the ionization source is a radioactive source, a corona source or a laser source.

Further, the ionization source is a corona pin.

Further, the asymmetric field ion mobility spectrometer can comprise a controller, for applying an asymmetric high voltage RF waveform and DC compensation voltage onto the electrode plate and the electrode filaments.

The above non-specific embodiments of the present invention at least bring about one or more of the following advantages and effects: increasing accuracy of identifying ion peak positions; reducing scanning time of DC voltage and types of the compensation voltage, thereby improving ion detection efficiency.

BRIEF DESCRIPTION OF THE DRAWINGS

These aspects and/or other aspects as well as advantages of the present invention will become obvious and readily understood from the description of the preferred embodiments of the present invention in conjunction with the accompanying drawings below, in which.

DETAILED DESCRIPTION OF THE EMBODIMENTS

Figure 1:
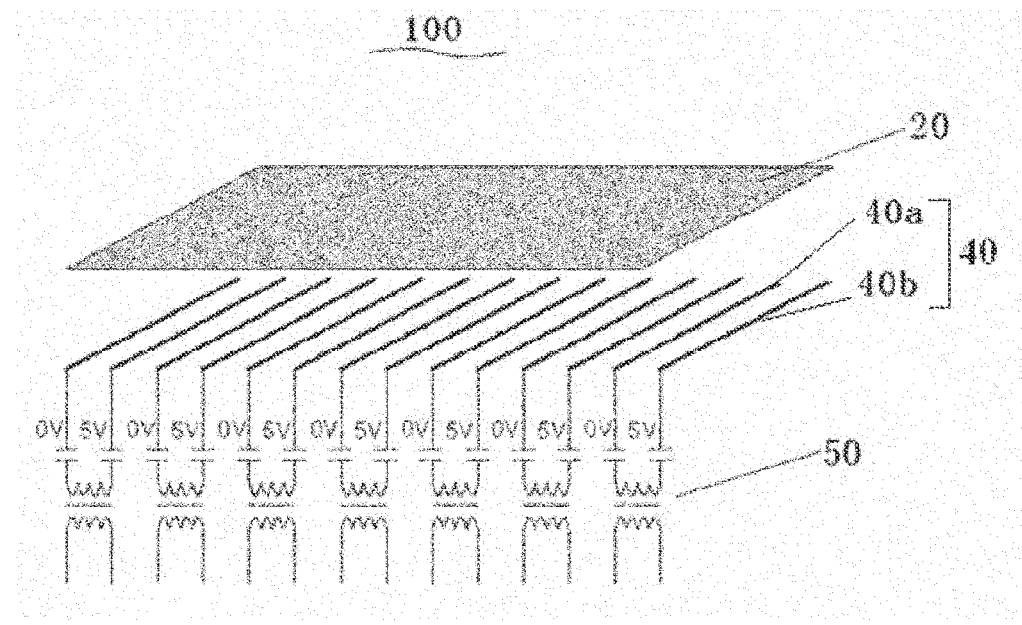
FIG. 1 is a structural schematic view of electrode structure in an asymmetrical field ion mobility spectrometer in accordance with an embodiment of the present invention.

The technical solution of the present invention will be further explained in detail, by the following embodiments, with reference to FIGS. 1-5c. Throughout the specification, the same or similar reference numerals will indicate the same or similar components. The explanation to the implementations of the present invention with reference to the accompanying drawing is intended to interpret the general inventive concept of the present invention, instead of limiting the present invention.

Figure 2:
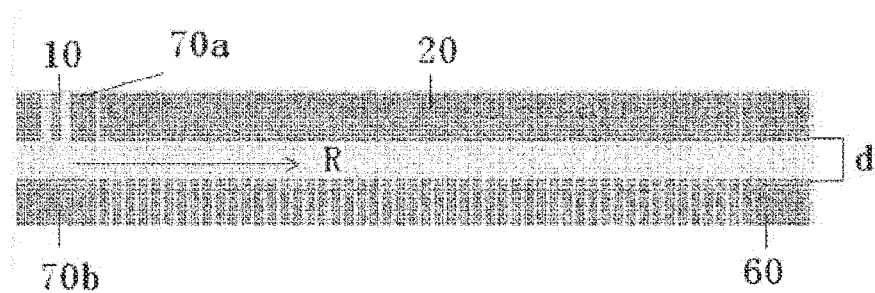
FIG. 2 is a schematic view of the electrode structure shown in FIG. 1 for use with an ionization source.

With reference to FIGS. 1 and 2, the present invention provides an asymmetric field ion mobility spectrometer 100 having a new electrode structure. It includes an ionization source 10 for generating ions; and an electrode plate 20. It also includes a plurality of electrode filaments 40, which are positioned in opposite to the electrode plate 20 and spaced apart from it by an analysis gap d. A high voltage electrical field is applied between the electrode filaments and the electrode plate so as to form an ion migration area R. The electrode filaments 40 are used to collect ions which do not pass through the ion migration area R. It further includes a collection electrode 60, arranged at a rear end of the ion migration area R, and for collecting the ions which have passed through the ion migration area R.

In one embodiment, the plurality of electrode filaments 40 can include at least one pair of reference filament 40a and signal filament 40b positioned adjacent to each other. The corresponding reference filament 40a and signal filament 40b in the pair are spaced apart with a predetermined distance (as shown) with each other. There is a certain potential difference between the corresponding reference filament 40a and signal filament 40b in each pair. Preferably, the respective reference filaments 40a and signal filaments 40b are arranged and spaced apart in one plane in an alternative manner. The skilled persons in the art will know that the electrode filament structure as described above can be manufactured by a method of tightening the filaments, etching the filaments and so on.

The corresponding reference filament 40a and signal filament 40b in each pair of the reference filament and signal filament are respectively connected to two ends at a same side of an inductive coupler 50 via capacitance, so that a signal about ions collected by each signal filament 40b can be picked up/extracted out at the other side of the inductive coupler 50. Further, a potential difference between the corresponding reference filament 40a and signal filament 40b in each pair can be equal to or less than 5V.

In one embodiment, the potential difference between the corresponding reference filament 40a and signal filament 40b in each pair can be equal to 5V. Specifically, the potential of the reference filament 40a can be 0V, and that of the signal filament can be +5V or −5V. The pair of the reference filament 40a and signal filament 40b as described above can be treated in a differential coupling so as to extract out the signal about the ions collected on the signal filament 40b (served as a collection filament). By such comparison and collection, charges are focused on each signal filament 40b, enhancing collection efficiency. As have been described above, up to thousands of RF electrical field will be applied on the electrode plate, causing very strong noise disturbance. As a result, only ions having measurable charge amount larger than the noise disturbance (i.e., meeting a certain requirement on signal-to-noise), can be identified. Due to this, the collection electrode in the prior art must be sufficiently large (for example, in a form of bulk) and the charge amount must be large enough to generate signal. However, such arrangement has a poor resolution, and typically it is not possible to perceive a shape of a weak. The electrode filament structure directly eliminates the high noise disturbance generated by RF electrical field by such comparison method. Therefore, the present invention can generate signal, even if the signal filament and the charge amount both are small, thereby improving resolving power. It can be seen from the result views of FIGS. 3-5c that distribution of peak shapes can be measured and the resolving power is improved.

It should be understood that the potential difference between the reference filament 40a and the signal filament 40b is not limited to the value as described above; and it can be selected by the skilled person in the art as required.

Specifically, with reference to FIG. 2, the asymmetric field ion mobility spectrometer 100 in accordance with the present invention further includes a pair of introduction electrodes 70a and 70b oppositely arranged at a front end of the ion migration area R. More particularly, the pair of introduction electrodes include an upper introduction electrode 70a and a lower introduction electrode 70b. The ionization source 10 is inserted into an immediate part of the upper introduction electrode 70a. In one embodiment, the ionization source 10 is inserted into a circular hole of the upper introduction electrode 70a from an upper side thereof.

In an embodiment of the present invention, the analysis gap can have a width of 0.5 mm, and the electrode filament can have a diameter in a range of 0.1-0.3 mm, and the spacing between respective adjacent electrode filaments can be 0.1-0.5 mm. In one embodiment, the electrode plate has a length of 15 mm, a width of 2 mm, and a height of 0.5 mm. Further, the electrode filament can have a diameter of 0.1 mm, and the spacing between the respective adjacent electrode filaments is 0.1 mm. The migration area has a length of 1.3 mm-11.2 mm. The spacing between the upper introduction electrode 70a and the electrode plate 20 is 0.1 mm.

The electrode plate 20 can be a copper plating layer which is plated on glass material or insulator, and the electrode filament 40 can be a copper filament or a copper filament plated on the insulator. The ionization source 10 can be a radioactive source, a corona source or a laser source. In one embodiment, the ionization source 10 is a corona pin. It should be noted that when the ionization source 10 employs a pulsed corona source or laser, it requires to generate ionized clusters having a small pulse width; and when the ionization source 10 is a radioactive source, it requires to achieve the pulsed ion clusters under a control of another electrode, while the generated ion cluster is very narrow along a longwise direction of the electrode plate.

In one embodiment, the asymmetric field ion mobility spectrometer in accordance with the present invention further may include a controller (not shown), to apply asymmetric high voltage RF waveforms and DC compensation voltage onto the electrode plate 20 and the plurality of electrode filaments 40.

With reference to FIGS. 3-5c, the operating principle of the asymmetric field ion mobility spectrometer of the present invention will be described next:

It can be known from the above that when the potential of the reference filament 40a is 0V, if the potential of the signal filament 40b is positive, the present ion mobility spectrometer can identify and recognize negative ions (negative ion working mode); and if the potential of the signal filament 40b is negative, the present ion mobility spectrometer can identify and recognize positive ions (positive ion working mode).

Figure 3:
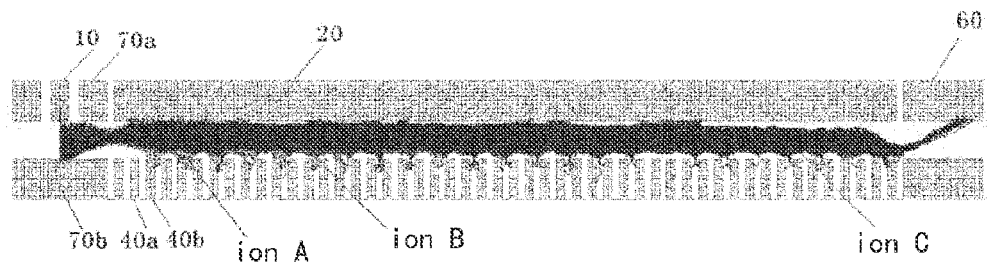
FIG. 3 is a view of simulation distribution result of three different ions A, B and C after passing through the electrode structure of FIG. 1.

Upon performing an ion identifying test, the ion source is disposed below the ionization source 10 as shown in FIG. 3, and the generated ion cluster is distributed along a longitudinal direction while the centre of the ion cluster is located in the middle of the upper and lower introduction electrodes 70a and 70b, exhibiting Gauss Distribution with 0.4 mm of FWHM (full width at half maximum). In the embodiment shown in FIG. 3, the ion cluster includes three kinds of negatively charged ions having molecular weights of 127, 227, and 327, respectively. The number of each kind of negatively charged ions is approximately 500.

Under the action of the electrical field, when the ion cluster passes through the gap between the upper introduction electrode 70a and the electrode plate 20, it is focused, and then enters the ion migration area having the analysis gap or width d of 0.5 mm. The lightest ions fall onto the signal filaments 40b at the front end of the ion migration area (i.e., the left side of FIG. 2, for example an entrance). The heavier ions fall onto the middle part of the ion migration area and the heaviest ions arrive at the collection electrode through the ion migration area.

As shown in FIG. 3, the ion A is the negative ion having a molecular weight of 127; the ion B is the negative ion having a molecular weight of 227 and the ion C is the negative ion having a molecular weight of 327. When the above three kinds of ions are emitted at the same time, they would fall onto different signal filaments 40b, forming a certain distribution. Different peak positions can be clearly identified from FIG. 4, thereby distinguishing three kinds of different ions having different molecular weights from each other.

Figure 5A:
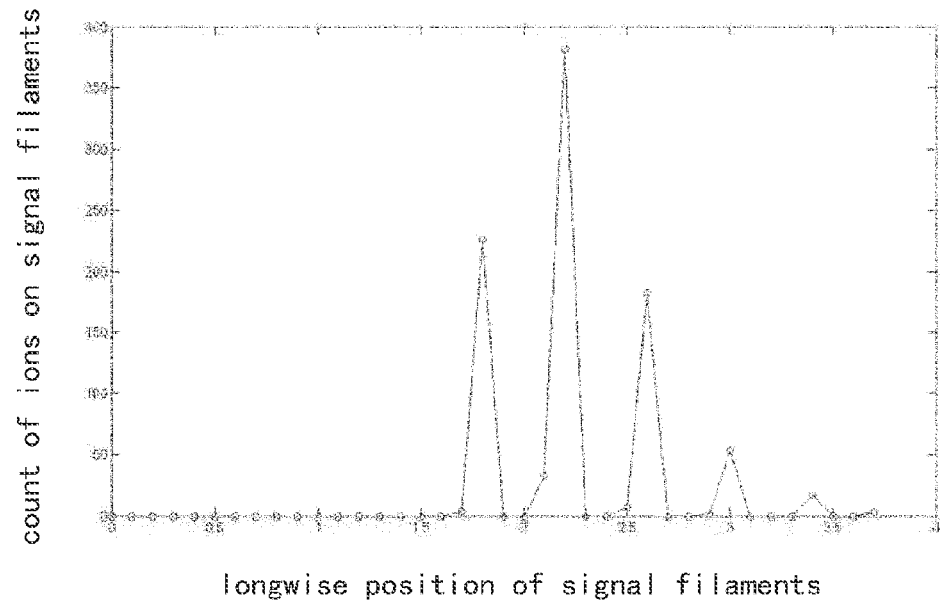
FIGS. 5a, 5b and 5c are respectively views of distribution results of ions A, B and C having molecular weights of 127, 227 and 327, falling on the electrode structure shown in FIG. 1.
Figure 5B:
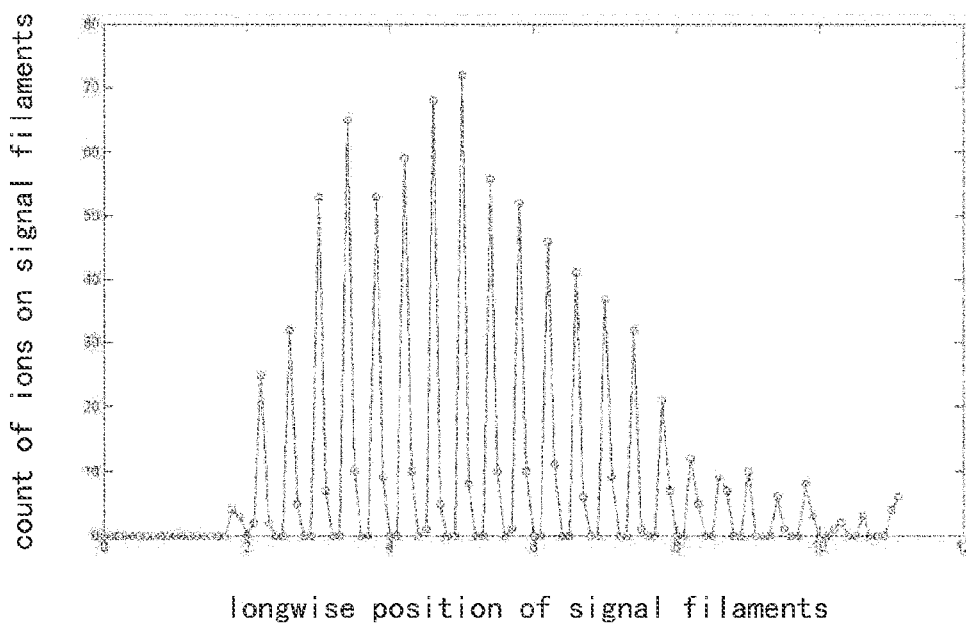
Figure 5C:
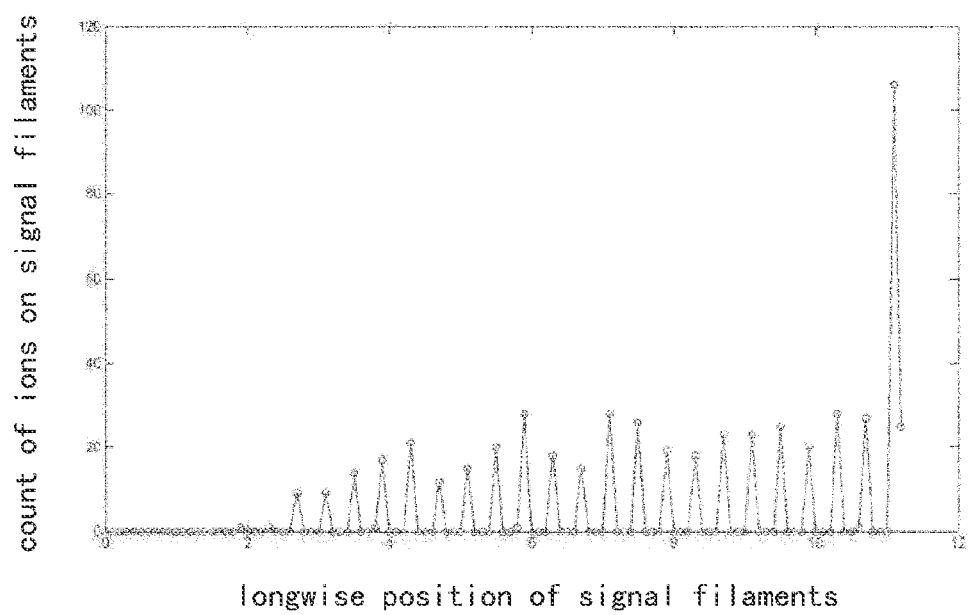

As shown in FIGS. 5a-c, they respectively illustrate the peak positions of the three kinds of ions on the signal filament 40b. Specifically, as shown in FIG. 5a, the peak position of the ions having the molecular weight of 127 (a displacement along the electrode filament in a longwise direction) is 2.2 mm, FWHM (full width at half maximum) thereof is 1 mm, and the ions fall on the signal filaments at the front end of the ion migration area. As shown in FIG. 5b, the peak position of the ions having the molecular weight of 227 is 5 mm, FWHM thereof is 4.5 mm, and the ions fall on the signal filaments at the middle part of the ion migration area. As shown in FIG. 5c, the ions having the molecular weight of 327 pass through the ion migration area and are collected by the collection electrode at the rear end of the ion migration area.

Figure 4:
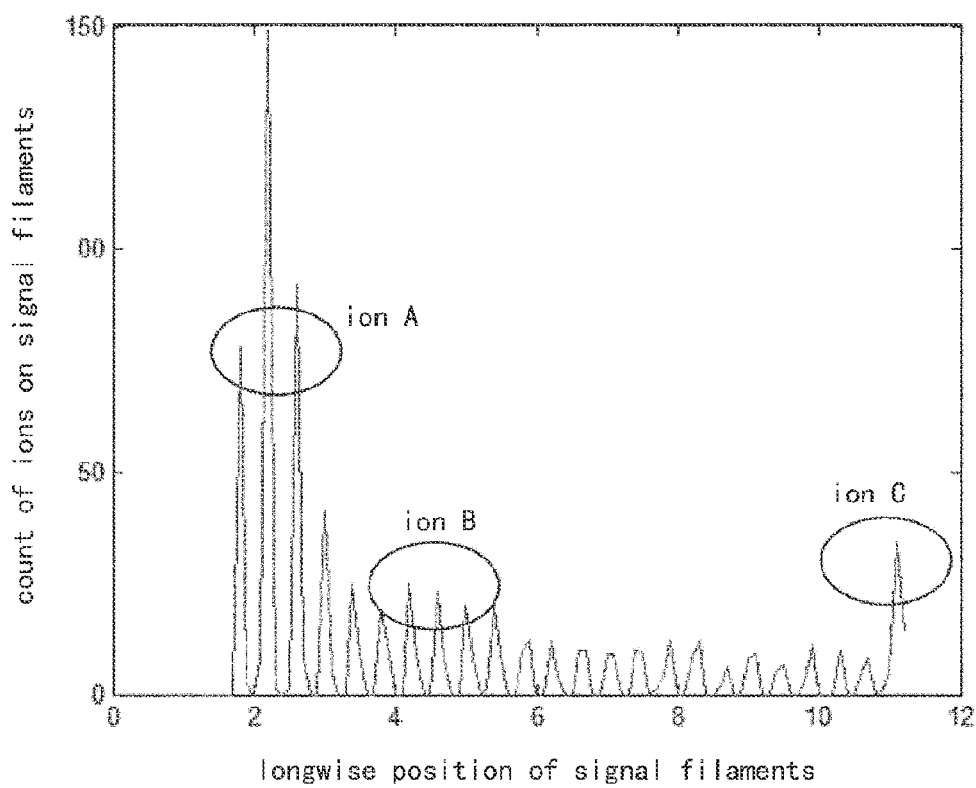
FIG. 4 is a view of ion distribution result of three different ions A, B and C captured on electrode filaments, wherein they are emitted at the same time.

Please be noted that FIGS. 4 and 5 are the views of the distribution result of the ions A, B, and C falling onto the signal filaments of FIG. 1 under the same condition. The difference of FIG. 4 from FIG. 5 lies in the count of ions A, B, and C by the signal filaments (i.e., the ordinates of FIGS. 4 and 5 are different from each other), while other conditions are identical. In other words, it can be seen from FIGS. 4 and 5 that although their counts on the ions A, B and C are different, both of them can clearly identify the peak positions of the ions A, B and C. Finally, they can obtain the same identification result (i.e., the same peak positions for ions A, B and C).

It should be understood that the views of FIGS. 4 and 5 are illustrative, and they are mainly intended to explain the fact that the asymmetric field ion mobility spectrometer as shown in FIG. 1 is capable of well identifying the peak positions of ions A, B and C.

By this method, it is possible to identify different kinds of molecules under one compensation voltage, effectively improving resolution of substances by the asymmetric field ion mobility spectrometer, and reducing the range of scanning voltage and shortening time. The asymmetric field ion mobility spectrometer in accordance with the present invention not only can collect the ions passing through the ion migration area, but also can collect and analyze the ion not passing though the ion migration area.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the claims and equivalents thereof.

What is claimed is:

1. An asymmetric field ion mobility spectrometer, comprising:
    an ionization source, for generating ions;
    an electrode plate;
    a plurality of electrode filaments, arranged in opposite to the electrode plate and spaced apart from the electrode plate by an analysis gap, wherein a high voltage of electrical field is applied between the electrode plate and the electrode filaments to form an ion migration area, and the electrode filaments are used to collect the ions that do not pass through the ion migration area; and
    a collection electrode, disposed at a rear end of the ion migration area, and collecting the ions that have passed through the ion migration area,
    the plurality of electrode filaments comprising at least one pair of reference filament and signal filament adjacent to each other, spaced apart from each other by a predetermined distance with a potential difference between them.

2. The asymmetric field ion mobility spectrometer as claimed in claim 1, wherein,
    the corresponding reference filament and signal filament in each pair of the reference filament and signal filament are respectively connected to two ends of an inductive coupler on the same side via capacitance, so that a signal about the ions collected by each signal filament is extracted out from the other side of the inductive coupler.

3. The asymmetric field ion mobility spectrometer as claimed in claim 1, wherein,
    the corresponding reference filament and signal filament in each pair of the reference filament and signal filament has a potential difference equal to or less than 5V between them.

4. The asymmetric field ion mobility spectrometer as claimed in claim 1, wherein,
    a potential of the reference filament is 0V, and a potential of the signal filament is +5V or −5V.

5. The asymmetric field ion mobility spectrometer as claimed in claim 1, wherein,
    it further comprises a pair of introduction electrodes oppositely located at a front end of the ion migration area, and the ionization source is provided in a middle part of one introduction electrode in the pair of introduction electrodes.

6. The asymmetric field ion mobility spectrometer as claimed in claim 1, wherein, the analysis gap has a width of 0.5 mm, the diameter of the electrode filament is 0.1-0.3 mm and the distance between the respective adjacent electrode filaments is 0.1-0.5 mm.

7. The asymmetric field ion mobility spectrometer as claimed in claim 1, wherein, the electrode plate is a copper plating layer which is plated on glass material or insulator, and the electrode filament is a copper filament or a copper filament plated on insulator.

8. The asymmetric field ion mobility spectrometer as claimed in claim 1, wherein, the ionization source is a radioactive source, a corona source or a laser source.

9. The asymmetric field ion mobility spectrometer as claimed in claim 8, wherein, the ionization source is a corona pin.

10. The asymmetric field ion mobility spectrometer as claimed in claim 1, wherein, It further comprises a controller, for applying an asymmetric high voltage RF waveform and DC compensation voltage onto the electrode plate and the electrode filaments.

* * * * *